(12) United States Patent
Buechi et al.

(10) Patent No.: US 9,517,321 B2
(45) Date of Patent: Dec. 13, 2016

(54) TUBE FOR A RESPIRATOR SYSTEM

(71) Applicant: Hamilton Bonaduz AG, Bonaduz (CH)

(72) Inventors: Rudolf Buechi, Chur (CH); Marc Maeder, Malans (CH); Axel Zolkos, Felsberg (CH)

(73) Assignee: Hamilton Bonaduz AG (CH)

( * ) Notice: Subject to any disclaimer, the term of this patent is extended or adjusted under 35 U.S.C. 154(b) by 377 days.

(21) Appl. No.: 14/358,128

(22) PCT Filed: Sep. 27, 2012

(86) PCT No.: PCT/EP2012/069149
§ 371 (c)(1),
(2) Date: May 14, 2014

(87) PCT Pub. No.: WO2013/072119
PCT Pub. Date: May 23, 2013

(65) Prior Publication Data
US 2014/0311487 A1    Oct. 23, 2014

(30) Foreign Application Priority Data
Nov. 17, 2011   (DE) .................. 10 2011 055 439

(51) Int. Cl.
*A61M 16/08* (2006.01)
*A61M 16/10* (2006.01)
(Continued)

(52) U.S. Cl.
CPC ..... *A61M 16/1095* (2014.02); *A61M 16/0003* (2014.02); *A61M 16/0051* (2013.01);
(Continued)

(58) Field of Classification Search
CPC ............ A61M 16/1095; A61M 16/109; A61M 16/0876; A61M 16/16; A61M 16/0816; A61M 16/08; A61M 16/1075; A61M 16/0883; A61M 16/0891; A61M 16/108; A61M 16/1085; A61M 39/10; A61M 2013/1022; G01K 2013/024
(Continued)

(56) References Cited

U.S. PATENT DOCUMENTS

2007/0079982 A1*  4/2007  Laurent ................. A61M 16/08
                                                              174/68.1
2012/0125333 A1*  5/2012  Bedford ................. A61M 16/06
                                                              128/203.25

FOREIGN PATENT DOCUMENTS

DE      202006007397 U1   9/2007
DE      102007003455 A1   8/2008

* cited by examiner

*Primary Examiner* — Bradley Philips
*Assistant Examiner* — Margaret Luarca
(74) *Attorney, Agent, or Firm* — Jansson Munger; McKinley & Kirby Ltd.

(57) ABSTRACT

A tube for a ventilation system (1) for newborns is provided with a first section (7) comprising a heating wire (14), an electrical conductor (15), and a first connector (9) and a second connector (10), and with a second section (8) comprising a heating wire (16) extending over at least a certain portion of its length, an electrical line (17) extending over at least a certain portion of its length, and a first connector (11) and a second connector (12), wherein the second section (8) comprises a temperature sensor (18), wherein the electrical and pneumatic connection of the first section (7) with the second section (8) via the connection of the second connector (10) of the first section (7) is achievable by either connecting to the first connector (11) of the second section (8), so that the second section (8) is substantially heatable, or by connecting to the second connector (12) of the second section (8), so that the second section (8) is substantially not heatable.

15 Claims, 2 Drawing Sheets

(51) Int. Cl.
*A61M 16/16* (2006.01)
*A61M 16/00* (2006.01)
*G01K 13/02* (2006.01)

(52) U.S. Cl.
CPC ........ *A61M 16/0057* (2013.01); *A61M 16/08* (2013.01); *A61M 16/0816* (2013.01); *A61M 16/0875* (2013.01); *A61M 16/109* (2014.02); *A61M 16/16* (2013.01); *G01K 13/02* (2013.01); *A61M 16/1075* (2013.01); *A61M 2205/3368* (2013.01); *G01K 2013/024* (2013.01)

(58) Field of Classification Search
USPC ........................................ 128/203.26, 203.27
See application file for complete search history.

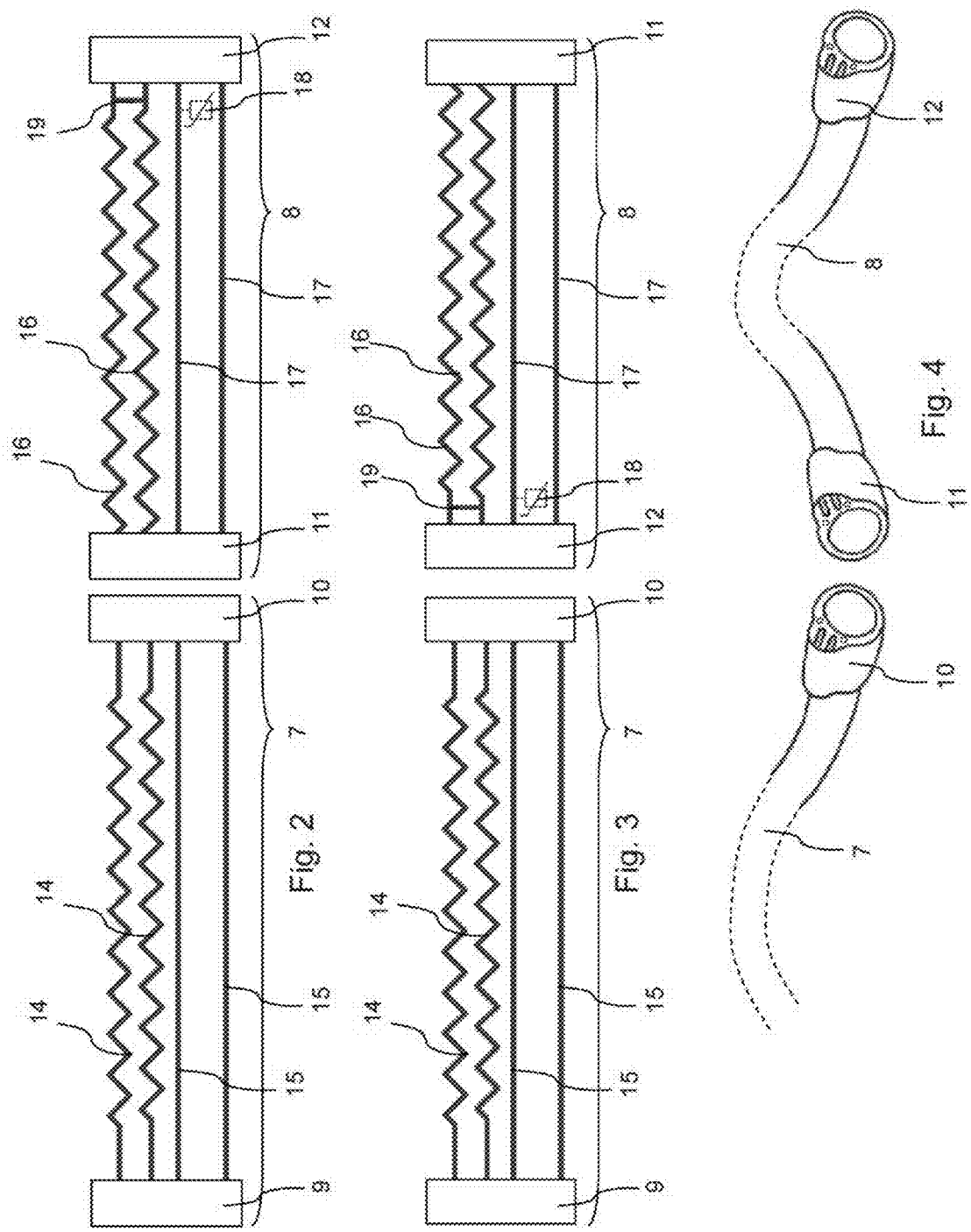

TUBE FOR A RESPIRATOR SYSTEM

FIELD OF INVENTION

The present invention pertains to a tube for a respirator system for ventilating patients with breathing gas, especially for a respirator system for newborns.

BACKGROUND OF THE INVENTION

During the mechanical ventilation of patients on an intensive-care ward, for example, the patient to be ventilated is connected pneumatically to the ventilation device by means of a breathing tube system. Because the breathing gas which is delivered to the patient must be adjusted with respect to temperature and humidity to the physiological needs of the patient, a respiratory humidifier is arranged in the inhalation or inspiration tube to heat and humidify the breathing gas. The respiratory humidifier comprises a liquid container filled with distilled water in the usual manner; the inhalation gas is conducted through this container, and its moisture content is thus increased.

To prevent moisture from condensing inside the breathing tube system, the inhalation tube and the expiration or exhalation tube are usually provided with electrical tube heaters, which heat the inhalation and exhalation gas flowing through them during operation. A loop of heating wire, for example, is used, which is integrated into the interior of the inhalation or exhalation tube, or the inhalation or exhalation tube is wrapped in each case with a coil of heating wire.

The breathing gas temperature is usually regulated by means of a temperature sensor arranged near the patient; this sensor is connected by an electrical measurement line to a control unit, which is arranged in, for example, the respiratory humidifier or in the ventilation device.

When newborns or infants are being ventilated in the neonatology department, there is the special circumstance that these patients are lying in incubators or humidicribs or warming beds, the temperature of which is usually kept at about 37° C. and thus above the temperature of the climate-controlled environment. For this reason, the area of the inhalation tube located inside the incubator or warming bed, for example, must be supplied with less heat or no heat at all, in contrast to the area of the tube located outside, which must continue to be heated to prevent condensation.

Previous approaches to the solution of this problem consisted, for example, in constructing the inhalation tube in such a way that the temperature sensor is attached at either one of two different positions on the tube depending on the application, that is, on whether an incubator is involved or a warming bed with radiation from an (infrared) heating lamp, and in using an additional, unheated piece of extension tubing at the end of the inhalation tube, upstream of the Y-piece.

Another approach is disclosed in DE 10 2007 003 455 A1, in which adapters are inserted into the inhalation and exhalation tubes; these adapters divide each of the overall heating sections into two heating subsections, one inside, the other outside the incubator. The two sections are heated independently of each other.

DE 20 2006 007 397 U1 describes a ventilation tube with different heating zones to deal with the different climate zones associated with infant incubators.

Solutions of this type are complicated to operate; they are also complex and thus lead to considerable cost. Because, for hygienic reasons, the system of tubing in ventilation systems frequently consists of medical-grade, single-use or disposable articles, approaches of this type do not lead to the goal envisioned here.

SUMMARY OF THE INVENTION

It is therefore the object of the present invention to provide a tube for respirator systems which can be produced at low cost, can be managed and applied flexibly and easily, and which makes it possible to provide reliable heating and thus proper ventilation under any application conditions.

This object is achieved by the features of claim 1. Advantageous designs and embodiments are the objects of the subclaims.

According to the invention, a tube for a ventilation system for newborns is provided with a first section, comprising a heating wire, an electrical line, and a first connector and a second connector; and a second section, comprising a heating wire extending over at least a certain part of its length, an electrical line extending over at least a certain part of its length, and a first connector and a second connector, wherein the second section comprises a temperature sensor; wherein the electrical and pneumatic connection of the first section is with the second section via the connection of the second connector of the first section is achievable by either one of two different alternative configurations: in a first configuration, wherein the second connector of the first section is connected to the first connector of the second section, so that the second section is heatable; or in a second configuration, wherein the second connector of the first section is connected to the second connector of the second section, so that the second section is substantially not heatable. Thus, the tube is usable as a combination of the first section with the second section in several configurations in a versatile manner. The entire tube or only a part of it can be heated without any change to the (external) settings of the heating system; that is, by simply turning the second section around (exchanging the connectors) the other heating configuration is achieved.

The tube is preferably configured as an inhalation tube, wherein the first section is connectable to a respiratory humidifier, and the second section is connectable to a Y-piece near the patient. This represents the standard application of the tube according to the invention. The alternative in which a tube according to the invention is also used as an exhalation tube is also conceivable.

The heating wire of the first section and/or of the second section is configured preferably as a high-impedance, two-wire line. Thus the two-wire line can be used as a resistance heater, which, for example, is integrated in spiral form into the wall of the tube. Alternatively, more than two high-impedance heating wires are also possible. Other configurations besides the spiral form can also be used, e.g., a longitudinal arrangement or a zigzag shape.

It is advantageous to configure the electrical line of the first and/or second section as a low-impedance, two-wire signal and measurement line and to integrate it into, for example, the wall of the tubing. This facilitates an easy connection of the temperature sensor or other sensors. Additional signal or measurement lines such as data transmission lines can also be present. The signal and measurement lines can be arranged parallel to the heating lines, for example. Alternatively, each of the lines can be (thermally) isolated from each other.

It is especially advantageous to configure the temperature sensor as a thermocouple and to integrate it into the second connector of the second section, wherein the thermocouple is adapted to bridge the low-impedance, two-wire signal or measurement line, and wherein a connection in the second connector of the second section is adapted to bridge the high-impedance heating wire line. This results in an especially simple structure of the second section, which can be easily turned around so that the tube can assume its other configuration. The integration of the thermocouple into the connector means that it is possible to select the optimal point for measuring the temperature. The bridging of the electrical connection in the second connector of the second section short-circuits the heating line and thus effectively prevents the second section from being heated when in the second configuration.

It is also advantageous to form the electrical contacts of the connectors in such a way that they cannot be touched unintentionally from the outside. This prevents the contacts from being short-circuited and thus prevents heat from being produced unintentionally or the signal or measurement line from being rendered nonfunctional. This also eliminates the danger of damage to the electrical contacts almost completely.

The first section is preferably longer than the second section.

A respirator system with an inhalation tube, an exhalation tube, and a tube as defined above is also an aspect of the present invention. A breathing tube system of this type is part of a respirator system and normally connects a ventilation device, a respiratory humidifier, and a Y-piece together in such a way that a patient can be ventilated.

It is especially advantageous to configure the ventilator tubing system as a medical-grade, single-use or disposable article. This takes account of the hygienic requirements in a hospital. For delivery, the entire ventilator tubing system, possibly also with the liquid container of the respiratory humidifier, is shrink-wrapped in a plastic sheet, and after use on a patient, it is removed and replaced. As a result of the flexibility with which the tube according to the invention can be used, the ventilator tubing system is suitable for various applications in neonatology and also for the ventilation of adult patients.

BRIEF DESCRIPTION OF THE DRAWINGS

The invention is explained in greater detail below on the basis of exemplary embodiments with reference to the attached figures:

FIG. 2 shows a schematic diagram of the preferred embodiment of the tube according to the present invention in a first configuration;

FIG. 3 shows a schematic diagram of the preferred embodiment of the tube according to the present invention in a second configuration; and FIG. 4 shows a schematic diagram of the connectors in an embodiment of the tube according to the present invention.

DETAILED DESCRIPTION

Figure 1:
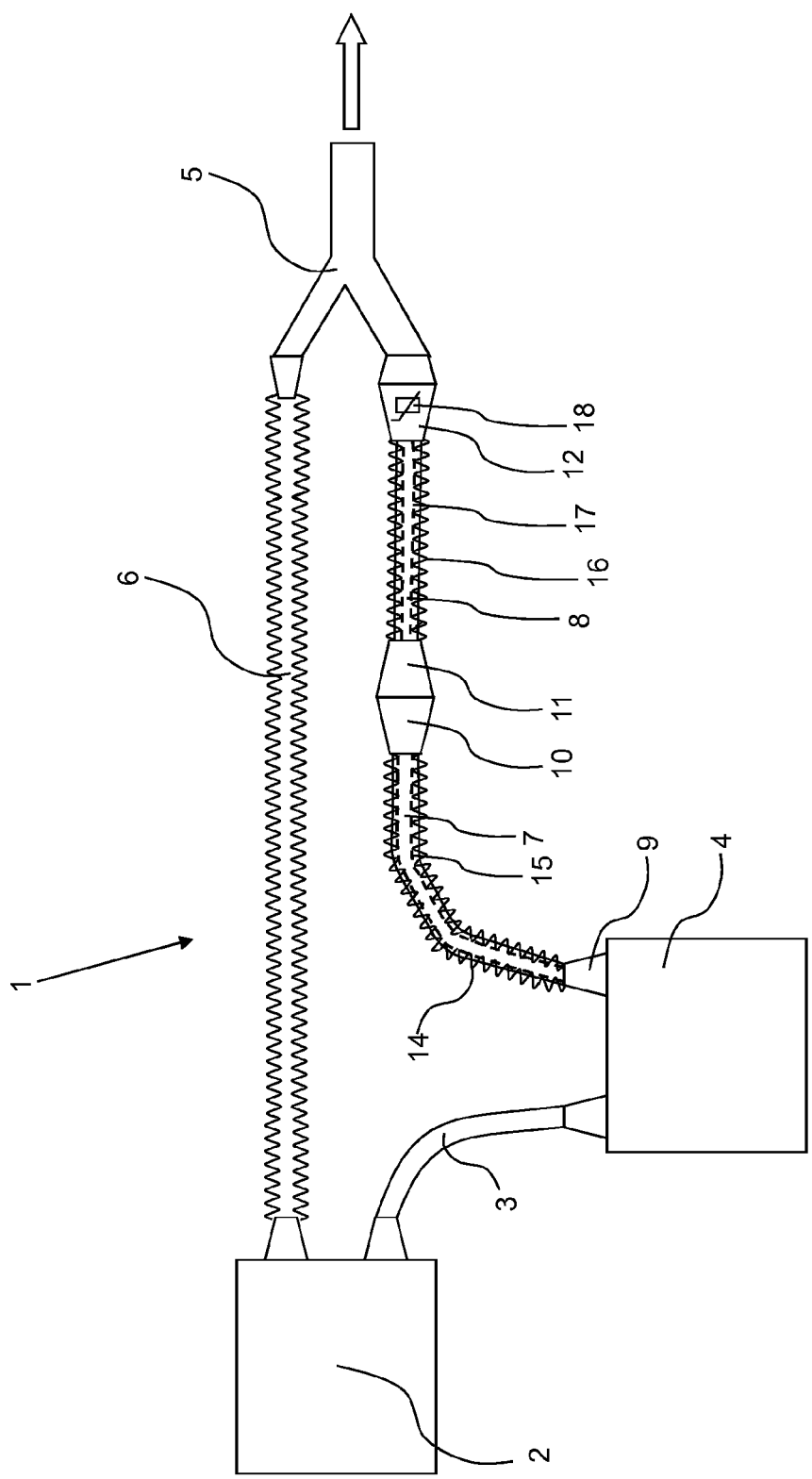
FIG. 1 shows a schematic diagram of a preferred embodiment of an inventive tube in a respirator system.

FIG. 1 shows a schematic diagram of a preferred embodiment of an inventive tube, which is used in a respirator system 1. A first inhalation tube 3 connects a respirator device 2 with a respiratory humidifier 4. The respiratory humidifier 4 is connected by the tube according to the invention to a Y-piece 5. The simply structured end of the Y-piece 5 points toward the patient to be ventilated, as indicated by the arrow. Finally, an exhalation tube 6 is arranged between the respirator device 2 and the other end of the Y-piece 5.

Dry breathing gas is produced in the respirator device 2 by, for example, a blower (not shown), leaves the device through the first inhalation tube 3, and arrives at the respiratory humidifier 4. There the breathing gas is conducted in the known manner into a liquid container (not shown in FIG. 1), where it is heated and humidified by a heated liquid such as distilled water. The heated and humidified breathing gas leaves the respiratory humidifier 4 through the tube formed by the combination of a first section 7 and a second section 8 and reaches the patient through the Y-piece 5. In correspondence with the breathing cycle controlled by the respirator device 2, the used breathing air leaves the patient again, enters the exhalation tube 6 at the Y-piece 5, and flows back to the respirator device 2.

In the first configuration shown here, the first section 7 is connected to the respiratory humidifier 4 by a first connector 9 and to a first connector 11 of the second section 8 by a second connector 10. A second connector 12 of the second section 8 connects this section to a connector of the Y-piece 5.

A heating wire 14 is integrated into the wall of the tubing of the first section 7; this wire is configured as a spiral-shaped, two-wire, high-impedance resistance heating coil. The power supplied to the heating wire 14 is provided by way of electrical connections in the first connector 9, which connects the first section 7 to the respiratory humidifier 4. Also integrated into the first section 7 is an electrical signal line 15, which is also of the two-wire type, that is, with two conductors, and which is able to transmit an electrical signal from the respiratory humidifier 4 to the second section 8 and/or in the opposite direction.

The second section 8 comprises a heating wire 16, which is usually configured as a spiral-shaped, two-wire, high-impedance resistance heating coil and which extends from the first connector 11 essentially all the way to the second connector 12. Integrated into the second section 8 is also an electrical signal line 17, which connects a thermocouple 18 arranged in the second connector 12 of the second section 8 electrically to the first connector 11. The measurement signal from the thermocouple 18 is transmitted from the connector 12 via the electrical signal line 17 to the connector 11 and from there via the connector 10, the electrical signal line 15, and the connector 9 to the control unit (not shown) of the respiratory humidifier 4. In other words: the connectors 10, 11 of the first and second sections 7, 8 are designed so that the corresponding electrical contacts connect the associated electrical heating and signal lines 14, 15, 16, 17 with each other, so that essentially a two-wire, high-impedance heating wire and a two-wire, low-impedance measurement or signal line is formed across both sections 7, 8. In this first configuration, the entire tube formed by the two sections 7, 8 is heatable, and the temperature is measured essentially at the end of the tube near the Y-piece 5.

In the case of the second configuration (not shown here), the second section 8 is arranged in exactly the opposite way; that is, the second connector 12 with the thermocouple 18 is connected directly to the second connector 10 of the first section 7; and the first connector 11 of the second section 8 is connected to the Y-piece 5. A short bridge line in the second connector 12 ensures that the heating wire 14 of the first section 7 is no longer electrically connected to the heating wire 16 of the second section 8, as a result of which the second section 8 is no longer heated. In similar fashion, an electrical line inside the second connector 12 connects the two elements of the electrical (two-wire) signal line 15 in such a way that the measurement signals from the thermocouple 18 can be transmitted. In the second configuration, therefore, only the first section 7 is heatable, and the temperature can be measured by the thermocouple 18 at the location of the second connector 12, essentially at the connecting point between the first and second sections 7 and 8.

The exhalation tube 6 can also comprise a tube heater in the form of a heating wire, which can also be configured as a spiral-shaped heating coil. The reason for heating the exhalation tube 6 is to prevent backflowing breathing gas from condensing in the exhalation tube 6 and from returning in the form of contaminated liquid, for example, to the patient via the Y-piece 5. The tube heater of the exhalation tube 6 can be configured as a continuous unit or in sections. According to the present invention, it is possible to use the two-part tube according to the invention as an exhalation tube. This increases the flexibility with which the ventilation system can be used even more.

FIG. 2 shows a schematic diagram of the tube according to the invention in the first configuration, that is, in the configuration like that shown in FIG. 1. The first section 7 comprises the two-wire, high-impedance heating line 14 and the low-impedance electrical measurement or signal line 15 extending between the first connector 9 and the second connector 10. The second section 8, which is shown somewhat shorter than the first section 7, comprises the two-wire, high-impedance heating wire line 16 and the low-impedance, electrical measurement or signal line 17 extending between the first connector 11 and the second connector 12. The temperature sensor 18, configured as a thermocouple, installed essentially on or in the connector 12, connects the two conducting elements of the electrical measurement or signal line 17, and the connecting piece 19, also shown schematically as a line and also installed essentially on or in the connector 12, connects the two conducting elements of the heating wire line 16.

The connection of connector 10 to connector 11 leads to the electrical contact of the elements of the heating wire line 14 with the corresponding elements of the heating wire line 16 and to the electrical contact of the elements of the electrical measurement or signal line 15 with the corresponding elements of the electrical measurement or signal line 17.

FIG. 3 shows a schematic diagram of the tube according to the invention in the second configuration, wherein the second section 8 has been turned around with respect to the first configuration; that is, its two connectors have changed places. The first section 7 is the same as that shown in FIG. 1. The second section 8, however, is now connected to the second connector 10 of the first section 7 by means of the second connector 12.

The temperature sensor 18, configured as a thermocouple, now measures the temperature essentially on or directly in the connector 12, wherein its measurement signal is transmitted via the electrical connection of the two connectors 12, 10 and the electrical measurement or signal line 15 of the first section 7 to the control unit (not shown), and the line shown schematically as a connecting piece 19 short-circuits the two conductor elements of the heating wire line 16 essentially at or in the connector 12 in such a way that no heating of the second section 8 can occur.

The connectors 10, 11 and 12 are configured in such a way that the turning-around of the second section 8 has no effect on the active electrical connections between the corresponding contacts. This can be achieved by suitable contact configurations of the known type. In particular, care must be taken to ensure that the connections between the connectors are easy to make and also easy to break; at the same time, sufficient measures must be taken to ensure the trouble-free transfer of the breathing gas. It would be possible to use screw type, rotary, plug-in type, spring type, or even magnetic connecting designs.

FIG. 4 shows a schematic diagram of the connectors in an embodiment of the tube according to the invention. The electrical contacts are arranged on the end surfaces of the connectors 10, 11, 12. It can be seen that the connectors 11 and 12 of the second section 8 are essentially symmetric in design, so that either one can be connected to the connector 10 of the first section 7.

The material of the tube or tubes, that is, the material of the inhalation tube 3, of the first and second sections 7, 8, and of the exhalation tube 6, comprises a suitable plastic such as polyethylene or polypropylene. Other suitable materials are also possible. The tubes are extruded or co-extruded by the known technique. The inside diameter of the tubes in a ventilation system for neonatology is usually about 12 or 15 mm, but larger diameters such as 19 mm or so can also be used in, for example, ventilation systems for adults. The connectors which form the transition between the tubes of the corresponding devices and the Y-piece 5 are also extruded from plastic material. Because strict requirements are imposed on these materials in the medical field, they must meet the requirements of ISO standard 5367-2000. As previously mentioned, the tube according to the invention is configured as part of a ventilation tube system and constitutes either a medical-grade single-use/disposable article or alternatively a reusable medical article, which can be returned to usable condition by washing and autoclaving. All components of the tube must be made in such a way that they cannot release any harmful compounds and are resistant to cold disinfectants such as CIDEX, Sekusept, Korsolex, etc.

The subject matter of the present invention thus provides a tube for a ventilation system for newborns which can be produced at low cost, can be used for many different purposes, and makes reliable heating and thus proper ventilation possible in any type of concrete application.

The invention claimed is:

1. A tube for a ventilation system for newborns comprising:
    a first section comprising a heating wire, an electrical line, and a first connector and a second connector; and
    a second section comprising a heating wire extending over at least a certain portion of its length, an electrical line extending over at least a certain portion of its length, and a first connector and a second connector, the second section including a temperature sensor; and
    electrical and pneumatic connection of the first section with the second section via the connection of the second connector of the first section being achievable by either one of two different alternative configurations, including (a) a first configuration in which the second connector of the first section is connected to the first connector of the second section so that the second section is heatable, or (b) a second configuration in which the second connector of the first section is connected to the second connector of the second section so that the second section is substantially not heatable.

2. The tube according to claim 1 wherein the first section is connectable to a respiratory humidifier and the second section is connectable to a Y-piece close to the patient.

3. The tube according to claim 1 wherein the heating wire of the first section and/or of the second section is formed as a high-impedance two-wire line.

4. The tube according to claim 1 wherein the electrical line of the first section and/or of the second section is formed as a low-impedance, two-wire signal or measurement line.

5. The tube according to claim 4 wherein:
the temperature sensor is configured as a thermocouple and is integrated into the second connector of the second section;
the thermocouple is adapted to bridge the low-impedance, two-wire signal or measurement line; and
a connection piece in or at the second connector of the second section is adapted to bridge the high-impedance heating wire line.

6. The tube according to claim 3 wherein:
the temperature sensor is configured as a thermocouple and is integrated into the second connector of the second section;
the thermocouple is adapted to bridge the low-impedance, two-wire signal or measurement line; and
a connection piece in or at the second connector of the second section is adapted to bridge the high-impedance heating wire line.

7. The tube according to claim 1 wherein the electrical contacts of the connectors are arranged on end surfaces thereof such that, when the connectors are connected end to end to each other, the electrical contacts are protected from being touched unintentionally from the outside.

8. The tube according to claim 1 wherein the first section is longer than the second section.

9. A ventilation tube system comprising:
an exhalation tube;
an inhalation tube upstream of a respiratory humidifier;
an inhalation tube downstream of the respiratory humidifier, such downstream inhalation tube including:
  a first section comprising a heating wire, an electrical line, and a first connector and a second connector; and
  a second section comprising a heating wire extending over at least a certain portion of its length, an electrical line extending over at least a certain portion of its length, and a first connector and a second connector, the second section including a temperature sensor;
electrical and pneumatic connection of the first section with the second section via the connection of the second connector of the first section being achievable by either one of two different alternative configurations, including (a) a first configuration in which the second connector of the first section is connected to the first connector of the second section so that the second section is heatable, or (b) a second configuration in which the second connector of the first section is connected to the second connector of the second section so that the second section is substantially not heatable.

10. A ventilation tube system according to claim 9 wherein at least the downstream inhalation tube is formed as a medical-grade, single-use or disposable article.

11. The ventilation tube system according to claim 9 wherein the first section is connectable to a respiratory humidifier and the second section is connectable to a Y-piece close to the patient.

12. The ventilation tube system according to claim 9 wherein the heating wire of the first section and/or of the second section is formed as a high-impedance two-wire line.

13. The ventilation tube system according to claim 9 wherein the electrical line of the first section and/or of the second section is formed as a low-impedance, two-wire signal or measurement line.

14. The ventilation tube system according to claim 13 wherein:
the temperature sensor is configured as a thermocouple and is integrated into the second connector of the second section;
the thermocouple is adapted to bridge the low-impedance, two-wire signal or measurement line; and
a connection piece in or at the second connector of the second section is adapted to bridge the high-impedance heating wire line.

15. The ventilation tube system according to claim 12 wherein:
the temperature sensor is configured as a thermocouple and is integrated into the second connector of the second section;
the thermocouple is adapted to bridge the low-impedance, two-wire signal or measurement line; and
a connection piece in or at the second connector of the second section is adapted to bridge the high-impedance heating wire line.

* * * * *